United States Patent [19]

Duncan et al.

[11] Patent Number: 5,677,532
[45] Date of Patent: Oct. 14, 1997

[54] SPECTRAL IMAGING METHOD AND APPARATUS

[75] Inventors: David B. Duncan, Auburn; Sherwood Kantor, Sacramento, both of Calif.

[73] Assignee: Duncan Technologies, Inc., Auburn, Calif.

[21] Appl. No.: 635,547

[22] Filed: Apr. 22, 1996

[51] Int. Cl.$^6$ .................................................. G01J 1/42
[52] U.S. Cl. .................................. 250/339.15; 250/330
[58] Field of Search .................... 250/339.15, 339.14, 250/330, 370.08, 339.01, 342; 340/578

[56] References Cited

U.S. PATENT DOCUMENTS

| | | |
|---|---|---|
| 3,553,665 | 1/1971 | Trumble . |
| 3,609,364 | 9/1971 | Paine . |
| 3,659,043 | 4/1972 | Low et al. . |
| 3,730,985 | 5/1973 | Whitney . |
| 3,742,124 | 6/1973 | Wilson et al. . |
| 5,168,528 | 12/1992 | Field, Jr. . |
| 5,169,233 | 12/1992 | Montgomery et al. . |
| 5,311,167 | 5/1994 | Plimpton et al. . |
| 5,547,369 | 8/1996 | Sohma et al. ............... 340/578 |

FOREIGN PATENT DOCUMENTS 2008717  1/1990  Japan .................. 250/339.15

OTHER PUBLICATIONS

J.D. Collins et al., "Miniature Hydrogen Fire Camera", I-Net Space Services, Published on the Internet, Sep. 1995.

National Aeronautics and Space Administration, "Dual Use Hydrogen Fire Camera", Feb. 13, 1996.

National Aeronautics and Space Administration, "Low-Cost, Handheld Hydrogen Fire Imager", Dec. 1995.

*Primary Examiner*—David P. Porta
*Assistant Examiner*—Richard Hanig
*Attorney, Agent, or Firm*—John P. O'Banion

[57] ABSTRACT

A fire detection camera and method of detecting fires which are not normally visible to the human eye. An image of the flame area is split into three light beams representing three different spectral ranges. The first beam corresponds to the flame image plus the background scene and is focused onto a first monochrome imaging device. The second beam corresponds to the background scene and is focused onto a second monochrome light imaging device. The third beam corresponds to light in the visible range and is focused onto a color imaging device to depict the visible surroundings. The background image is subtracted from the flame image to isolate the flame, and the isolated flame image is superimposed onto the color scene to depict a composite image that represents the flame in its actual surroundings.

12 Claims, 7 Drawing Sheets

SPECTRAL IMAGING METHOD AND APPARATUS

This invention was developed under Contract No. NAS13-669 with the National Aeronautics and Space Administration. The Government has certain rights in this invention.

BACKGROUND OF THE INVENTION

1. Field of the Invention

This invention pertains generally to spectral imaging, and more particularly to a method and apparatus for detecting fires wherein the flames are not visible to the human eye.

2. Description of the Background Art

Most combustion processes produce radiant energy. However, in the case of combustion of certain gasses, such as hydrogen, the radiation is in the near-infrared (IR) rather than visible portion of the spectra. As a result, fires involving such gasses are particularly dangerous. For example, the combustion of hydrogen results in a fire that, in addition to the usual dangers of any fire, has the added danger that it is not visible to the human eye. This presents a hazard to life and property at facilities where hydrogen is produced, stored, or utilized.

The spectra of a hydrogen fire is well characterized and this data has been applied to identify methods of producing a visible image of the fire. The most common approach is to image the strong IR emissions between 1300 nm and 1600 nm with the use of IR detectors. However, while this approach provides an image of the flame, there are disadvantages to the technique. For example, typical IR imaging systems produce an output image based solely on emissions in the IR wavelengths. Since there are many sources of IR emissions in any scene, the resulting IR image includes other components in addition to the flame. Furthermore, the relative intensities of IR radiation in a scene may be very different than the visible radiation. As a result, conventional IR imaging may produce an image in which the scene components may be difficult for the viewer to interpret. In addition, the technologies needed to perform IR imaging are relatively expensive.

Examples of conventional spectral imaging systems can be found in several U.S. patents. For example, U.S. Pat. No. 5,168,528 issued to Field, Jr. on Dec. 1, 1992 discloses a differential electronic imaging system. U.S. Pat. No. 3,742,124 issued to Wilson et al. on Jun. 26, 1973 discloses a color infrared detecting set. U.S. Pat. No. 3,730,985 issued to Whitney on May 1, 1973 discloses a viewing and measuring system for remote thermal energy sources. U.S. Pat No. 3,609,364 issued to Paine et al. on Sep. 28, 1971 discloses a hydrogen fire detection system with logic circuit to analyze the spectrum of temporal variations of the optical spectrum. U.S. Pat. No. 3,659,043 issued to Low et al. on Apr. 25, 1972 discloses a hydrogen fire blink detector. U.S. Pat. No. 5,311,167 issued to Plimpton et al. on May 10, 1994 discloses an UV/IR fire detector with dual wavelength sensing IR channel.

As indicated above, spectral imaging systems that can view infrared radiation generally require expensive hardware and detectors, and the image which is generated from conventional spectral imaging systems is very different from the visible scene. While the less expensive charge coupled device (CCD) arrays used in commercially available video cameras are also sensitive to light in the near-IR wavelengths, most CCD arrays are optimized for peak sensitivity in the visible wavelengths with sensitivity tailing off to nearly zero around 1200 nm. In typical video applications, IR response degrades the image quality and IR filters are frequently integrated with the array or the optical path to reduce the camera's IR response. If the IR filter is removed and the input light is filtered to detect one of the hydrogen flame spectral peaks at 900–940 nm or 1100–1150 nm, many video cameras will produce an image that includes the hydrogen flame emissions. However, there are many other sources of radiation in these spectral ranges, one of the strongest being sunlight. Therefore, a camera system based on simple filtering has no way to distinguish between radiation from a hydrogen fire and other sources of radiation or reflections of radiation.

As a result of the cost, complexity, and inaccuracies inherent in conventional flame monitoring equipment, "low tech" approaches such as waving a straw broom in the air around hydrogen handling equipment are commonly used to detect the presence of fires which are not visible to the human eye. If an invisible hydrogen fire is present, the broom will ignite and produce visible thermal radiation. Clearly, however, this is not an ideal solution to the problem.

Therefore, there is a need for a cost effective, easy to use, and accurate method and apparatus which can isolate a graphic image of a fire and overlay it onto a standard color video of the visible scene where the fire is located. The present invention satisfies this need, as well as others, and overcomes the deficiencies found in conventional flame monitoring equipment.

SUMMARY OF THE INVENTION

The present invention generally comprises a fire detection camera and method of detecting fires. In general terms, the invention isolates a graphic image of a burning gas which is not otherwise visible to the human eye and overlays the image onto a standard color video of the visible scene where the burning gas is located.

By way of example, and not of limitation, the spectral radiation resulting from hydrogen combustion has strong molecular emission peaks in the near infrared range which can be used to identify the flame; that is, smaller peaks around 930 nm and stronger peaks around 1100 nm. In accordance with the present invention, an image of the flame area is split into three light beams comprising three different spectral ranges. One beam comprises light which is either a band around 930 nm or above 1100 nm and represents the flame image plus the background scene. This output is focused onto a first monochrome CCD imaging device. A second beam comprises light which is outside the range of the hydrogen flame and represents the background scene only. This output is focused onto a second monochrome CCD imaging device. The background image (background only) is then subtracted from the flame image (background plus flame) to isolate the flame. While this information may be useful at his point, much of its value is lost without the surrounding visual information to provide data on the flame's location. Therefore, a third beam which comprises light in the visible range is focused onto a color CCD imaging device. The isolated flame image is then superimposed onto the color scene to depict a composite image that represents the flame in is actual surroundings.

An object of the invention is to detect flames which are not visible to the human eye.

Another object of the invention is to spectrally isolate radiation produced by a flame from background spectral radiation.

Another object of the invention is to provide a viewable image of a flame which is not visible to the human eye superimposed on an image of the surroundings in which the flame is present.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only.

DESCRIPTION OF THE PREFERRED EMBODIMENTS

Referring more specifically to the drawings, for illustrative purposes the present invention is embodied in the apparatus and method generally shown in FIG. 1 through FIG. 8. It will be appreciated that the apparatus may vary as to configuration and as to details of the parts, and that the method may vary as to the steps and their sequence, without departing from the basic concepts as disclosed herein.

Because of the particular hazards associated with hydrogen fires, the description herein refers to detecting and imagining of hydrogen fires using CCD arrays. However, it will be appreciated that, by adjusting the wavelength ranges processed by the spectral imaging apparatus and method described herein, many other types of fires or spectral emissions can be monitored. It will also be appreciated that the invention is not limited to using CCD arrays, and that other spectral detectors can be employed.

1. Spectral Imaging Method

Figure 1:
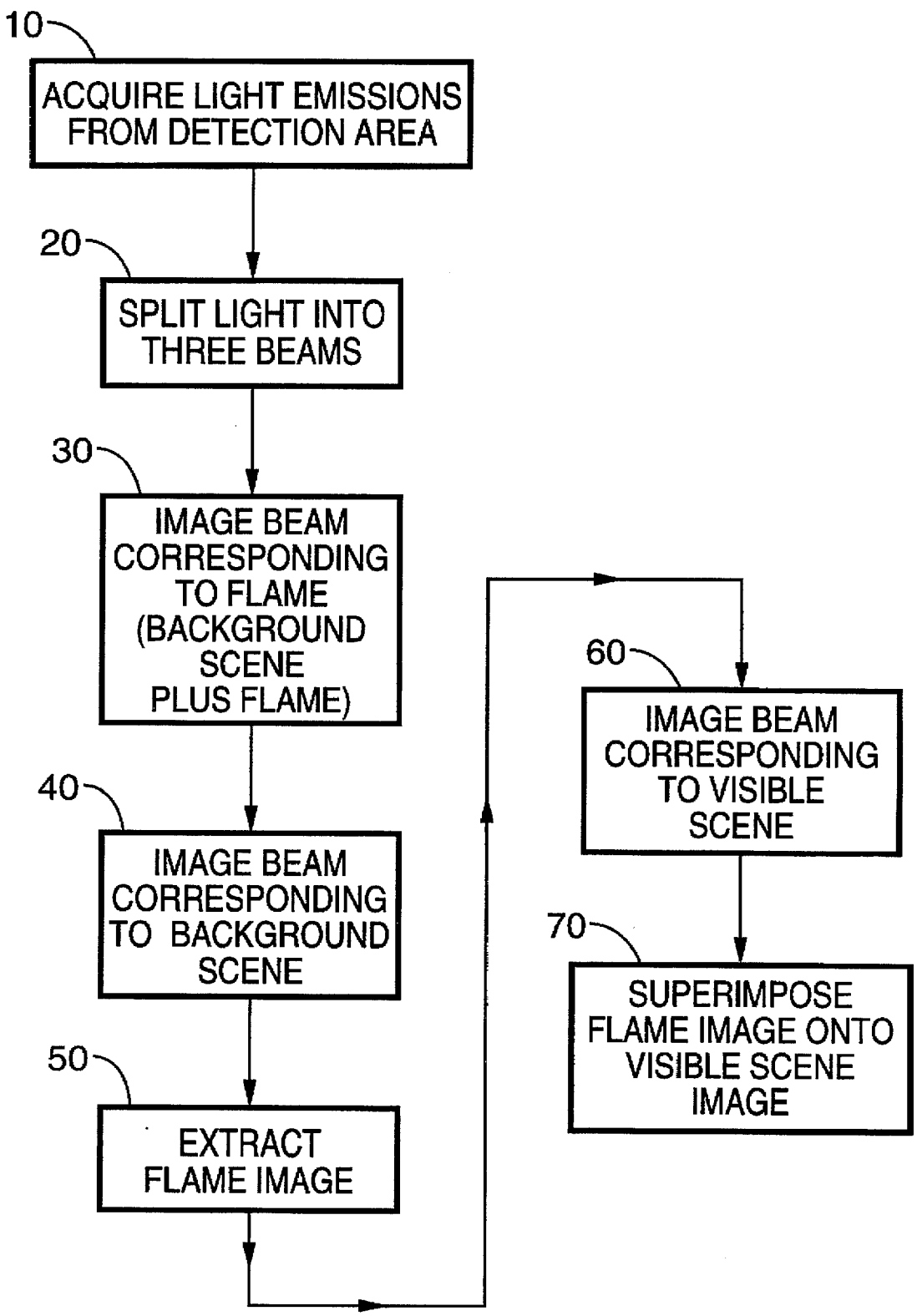
FIG. 1 is a flow charting showing a spectral imaging method in accordance with the present invention.

Referring first to FIG. 1, a spectral imaging method in accordance with the present invention is generally shown. At step 10, light emissions from the flame detection area are acquired. At step 20, the light acquired from the flame detection area is split into three light beams comprising three different spectral ranges. The first beam corresponds to the combined background scene and flame image; the second beam corresponds to the flame background scene only; and the third beam corresponds to the visible scene. At step 30, the beam representing the flame image plus the background scene is focused onto a first monochrome CCD imaging device. At step 40, the beam representing the background scene only (light outside the range of the flame) is focused onto a second monochrome CCD imaging device. At step 50, the background image (background only) is subtracted from the flame image (background plus flame) to isolate the flame. At step 60, the beam representing the visible scene is focused onto a color or monochrome CCD imaging device. At step 70, the isolated flame image is then superimposed onto the color scene to depict a composite image that represents the flame in is actual surroundings.

2. Flame Extraction/Image Processing

Figure 2:
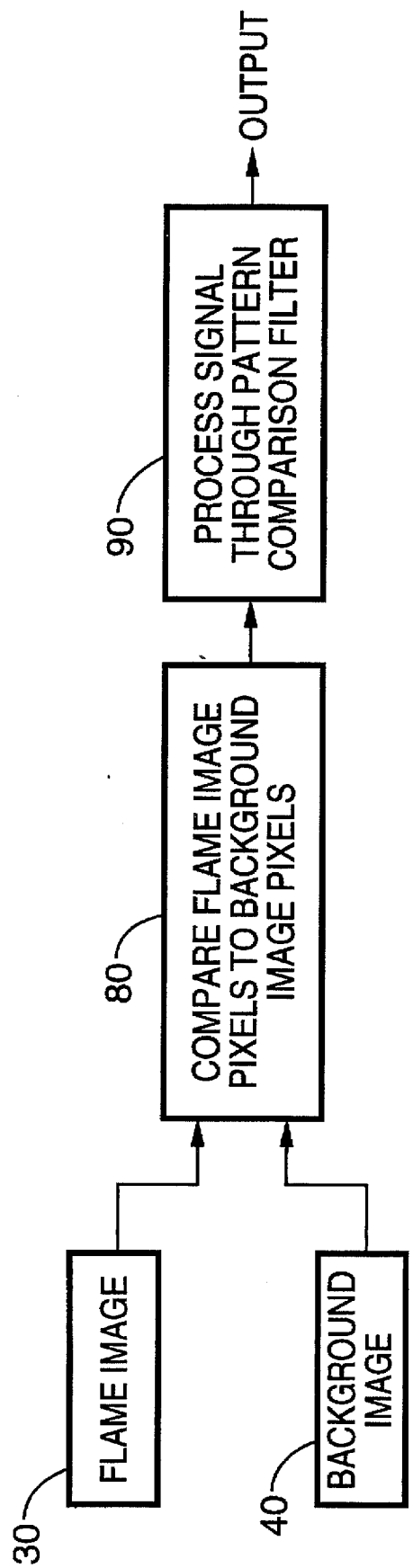
FIG. 2 is a flow chart showing a flame extraction method in accordance with the present invention.

The signals from the flame and background CCDs must be processed in order to identify which pixels are a pan of the flame image. In general, this process comprises subtracting the background image from the background plus flame image as described above. Referring also to FIG. 2, preferred flame extraction process corresponding to step 50 in FIG. 1 is shown with more particularity. At step 80, the flame image pixels (background plus flame) from step 40 are compared to the background image pixels (background only) from step 30 on a pixel by pixel basis. If the flame signal amplitude is greater than the background signal, it is assumed that the pixel is a flame pixel. This comparison results in a digital data stream signal that represents the presence of flame image pixels. The comparison is accomplished using a conventional high speed analog comparator which generates a logical "one" level output when the flame signal is greater than the background signal and a logical "zero" otherwise. When a flame pixel is detected, it's signal level is optionally forced to a preset high value to cause the flame image to be emphasized by forcing all of the flame pixels to the same bright value. Note also that, depending on the application, it may be useful to map flame pixel intensity to a set of gray values instead of a constant value so that the information portraying variation in flame intensity is not lost. Likewise, the flame pixels may be mapped to a given color in the final output signal to make it's presence easier to identify in the final image.

Figure 3:
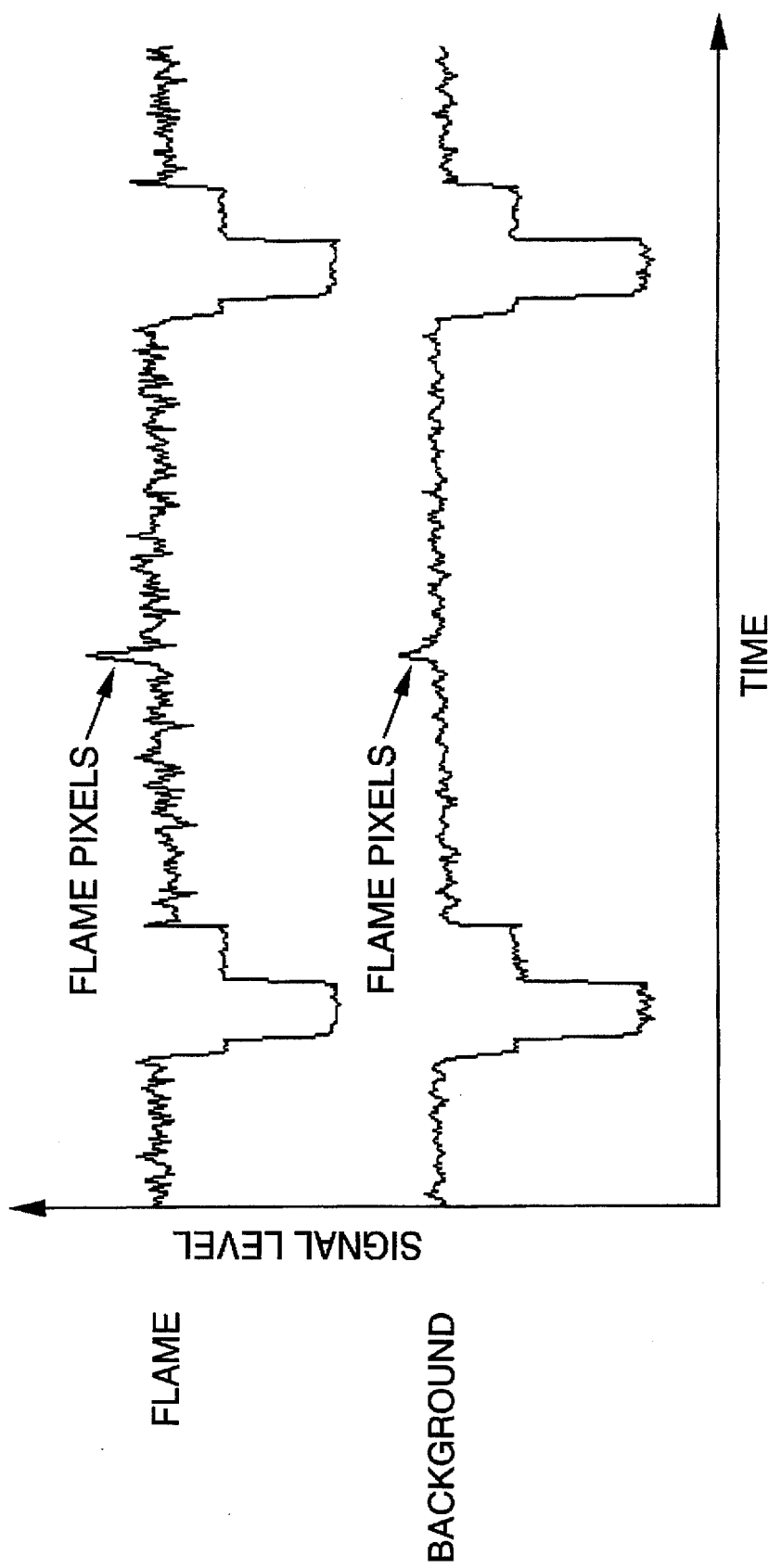
FIG. 3 is a graph comparing typical unprocessed flame and background composite video signals generated with an apparatus in accordance with the present invention when imaged on a flame positioned in front of a uniform background.

Due to the differences in the CCD arrays, electronics, and available light, the background and flame signals will not be entirely identical in the areas where there is no flame present. These differences can cause the comparison process to erroneously flag a flame pixel. Typically these "noise" pixels will occur as small dots in the image and vary from one to a few pixels in width. When a true flame is present, the flame image will generally be several pixels wide in any given row. This distinction is used by the camera's filtering process to remove erroneous pixels. FIG. 3 shows typical unprocessed composite video signals generated by the flame and background CCDs when imaged on a flame positioned in front of a uniform background. In FIG. 3, the upper trace represents the flame composite video whereas the lower trace represents the background composite video. The video signal resulting from processing the flame and background signals through at step 80 is shown in the upper trace of FIG. 4. Note the large number of "noise" pixels present in the video signal.

Figure 4:
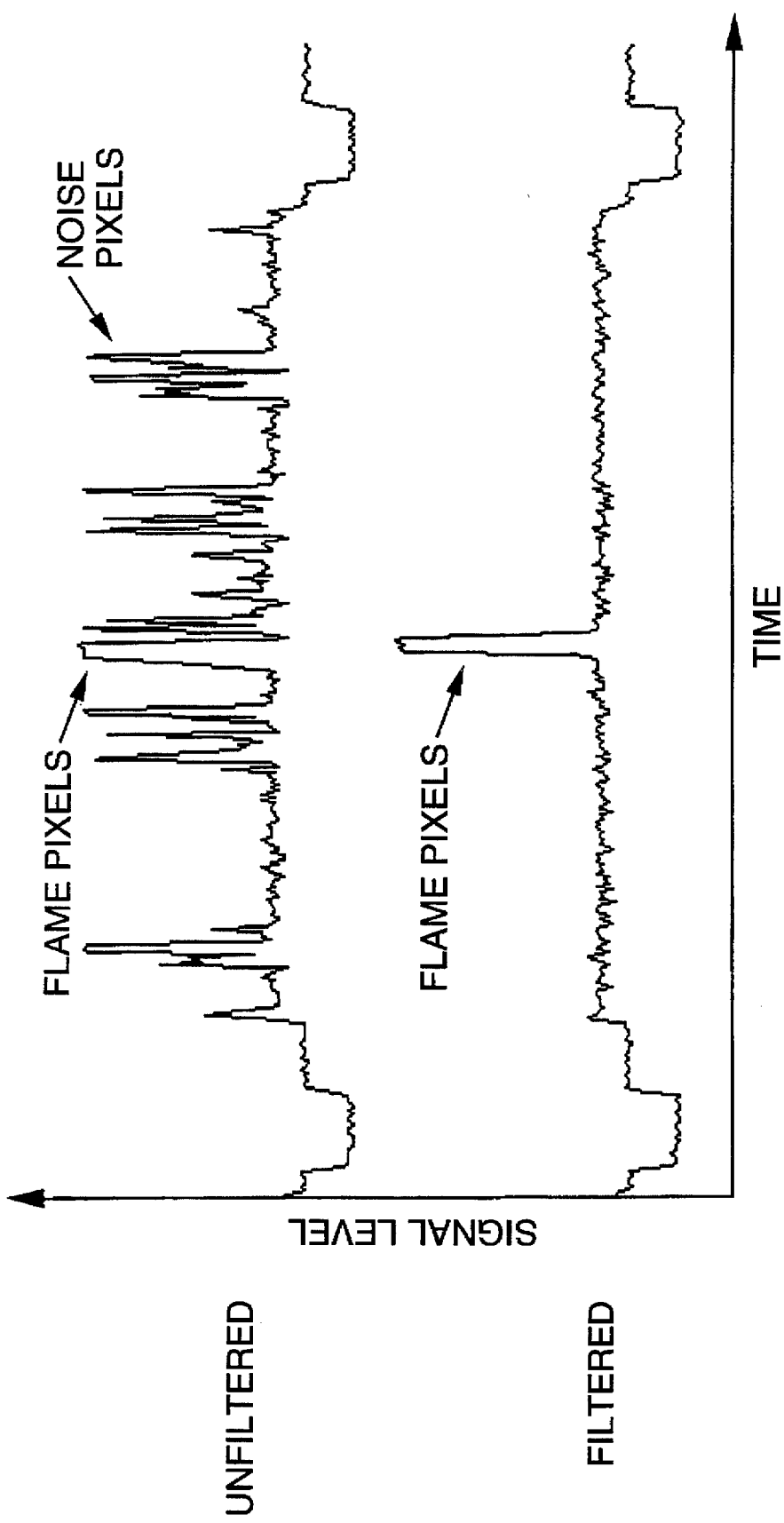
FIG. 4 is a graph comparing composite video resulting from processing the flame and background signals shown in FIG. 3 in accordance with the present invention, with and without pixel filtering in accordance with the present invention.

The lower trace of FIG. 4 shows the noise reduction resulting from processing the video signal from step 80 using a pixel filter for pattern comparison at step 90. This filtering, which is performed after the comparison between the flame and background signals, uses a one-dimensional single pixel digital filter which operates on sequential pixels in a single line. The digital filter is designed to pass the logical "one" comparator output signals from step 80 only when they are two or more pixels in length. Test results show a very significant post-filtering reduction of noise in the composite video output using this method. However, it will be appreciated that the filtering process can be extended to remove larger groups of noise pixels by increasing the number of pixels filtered. For example, the filter may use a five by five pixel window to compare the thresholded pixels to predefined patterns and remove any pixel groups that are less than three pixels square. In order to accomplish this extended filtering, the camera circuitry must include storage for a number of sequential rows of pixels equivalent to the dimension of the filter.

3. Hydrogen Flame Detection Method

In order to produce an image that is easily interpreted by a human viewer, a fire detection camera apparatus in accordance with the present invention must be able to indicate the presence of a hydrogen fire by marking pixels in a scene in a manner that indicates the location and size of the fire in a manner similar to the way flames typical of hydrocarbon based combustion might appear to the human eye. At the same time, all non-flame pixels of the image should remain as they would in any visible image.

When no hydrogen fire is present, light from any scene may include emissions in the IR and near-IR regions. This radiation may be considered a "background" signal. If a hydrogen fire is present, emissions from the fire are added to the background emissions, and any IR signal measured is actually the sum of the contributions from the background and fire emissions. Therefore, to isolate the flame emissions, the component of the signal produced by background emissions must be removed from the measured emissions.

To achieve the best indication of the presence of hydrogen fire, the combined flame and background signal should preferably be measured at a wavelength that corresponds to a maximum in the flame spectra. Furthermore, by making the measurement at a wavelength that also corresponds to a minimum in the spectra of solar radiation, the background contribution from sunlight can be minimized.

Figure 5:
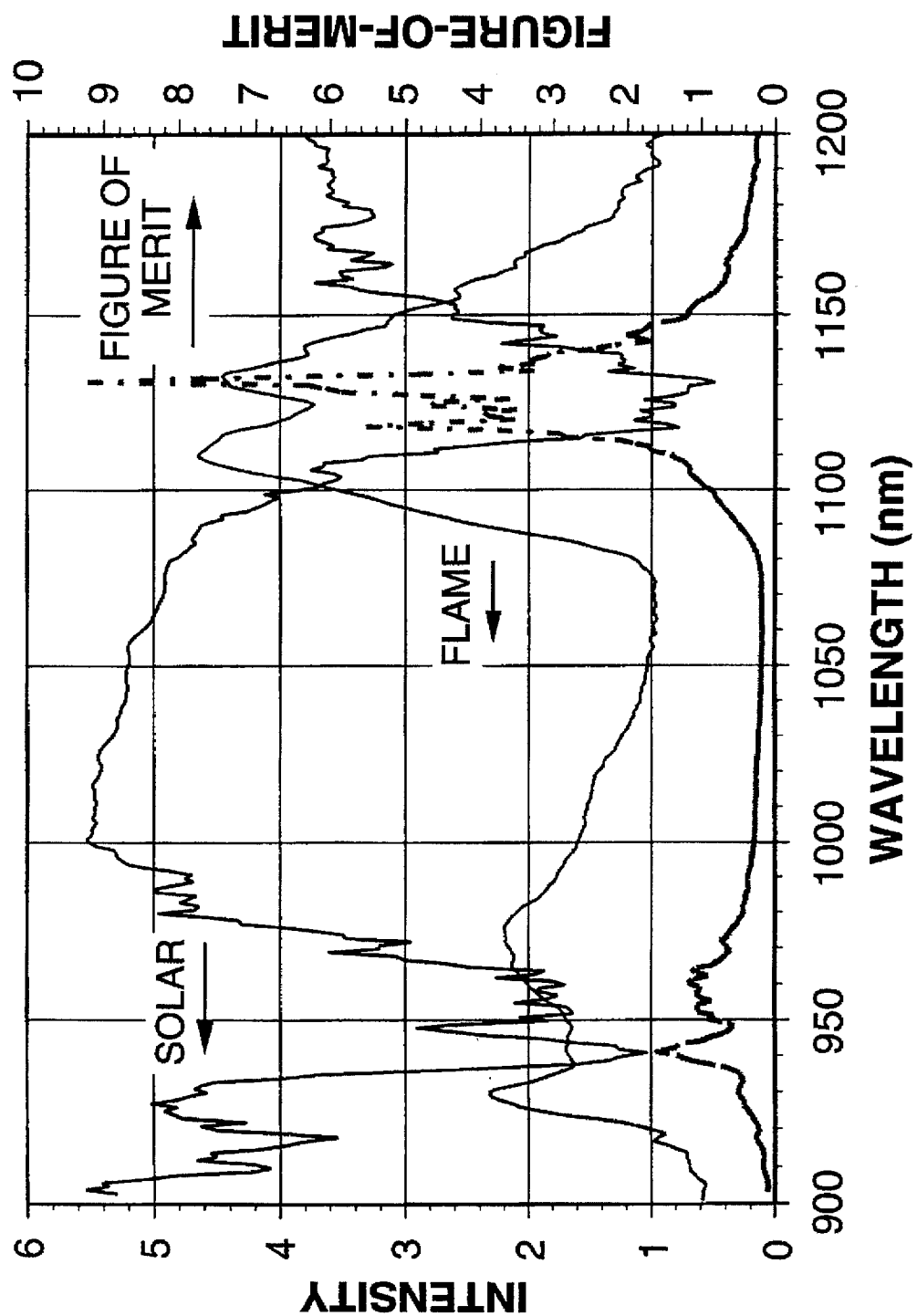
FIG. 5 is a graph comparing hydrogen flame and solar spectra in terms of intensity and figure of merit as functions of wavelength.

Referring to FIG. 5, the wavelength dependence of solar and hydrogen flame spectra in the 900–1200 nm region can be seen. A "figure-of-merit" plot indicates the ratio of the signal strength of a hydrogen flame to the solar radiation at any given wavelength. Those wavelengths with the highest figure of merit indicate spectral regions that will produce a measurement with the largest relative signal contribution from the flame emissions. The figure-of-merit signal is highest at 1130–1140 nm due to the strong atmospheric absorption of solar radiation in this spectral region.

In order to quantify the portion of the combined flame and background signal that is produced by background sources, a measurement is made in a spectral region where emissions from the flame are at a minimum. This background measurement is preferably in a region spectrally close to the combined flame and background measurement wavelength so that the signal intensity due to background emission sources will be similar in both measurements. As seen in FIG. 1, the wavelength region between 1030 nm and 1070 nm will provide a good background region that is spectrally adjacent to the flame measurement but where the flame intensity is minimal. Making the flame measurement in the region above 1110 nm offers the best flame viewing potential. Another peak occurs at 930 nm. Although the flame signal is less intense at this wavelength, the CCD arrays have a higher sensitivity in this region, making it a reasonable alternative for flame imaging.

When the intensity of the background signal and the combined flame/background signal are compared, any instance when the combined signal is larger than the background signal should indicate the presence of a hydrogen flame. Performing this comparison on a pixel by pixel basis allows the isolation of pixels that represent the location and intensity of the flame. All non-flame pixels can be ignored and replaced with a black pixel. This method will result in the production of an isolated image of the flame. The quality of the flame image can then be further enhanced by artificially increasing the relative brightness of flame pixels once they have been isolated.

It will be further appreciated that any differences in the magnitude of the background and combined flame/background signals that are caused by other sources such as electronic noise or differences in the CCD array detector response can cause erroneous indication of flame presence. Therefore, a spectral imaging apparatus in accordance with the present invention can be fitted with filters and the like to identify and eliminate these erroneous pixels.

To produce the final combined output image of the camera, the flame image is overlaid on the image resulting from a CCD array measuring the input light in the visible spectra. For all pixels where there is no flame pixel present, the visible image pixel intensity is displayed resulting in a combination of the two images.

3. Optical Implementation

Figure 6:
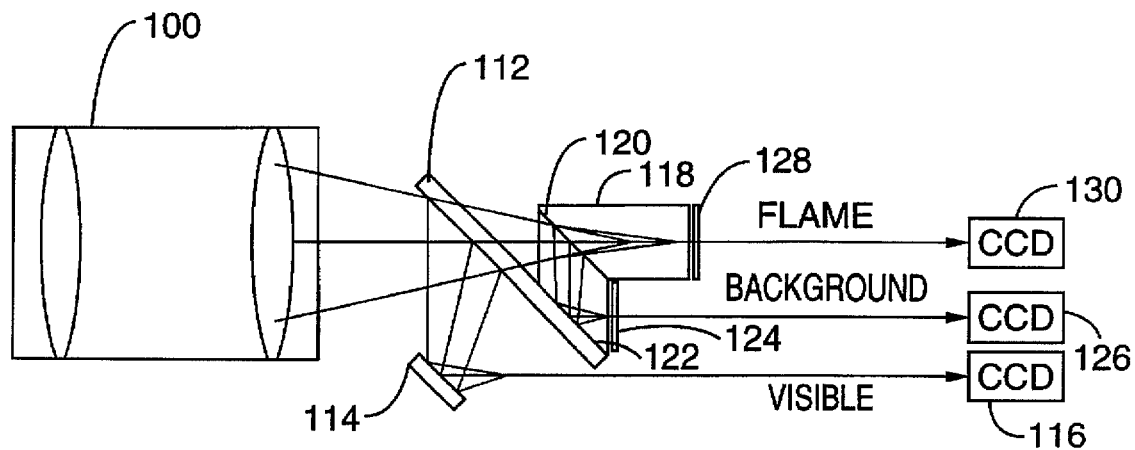
FIG. 6 is a functional schematic diagram showing an embodiment of the beam splitting optics in accordance with the present invention.
Figure 7:
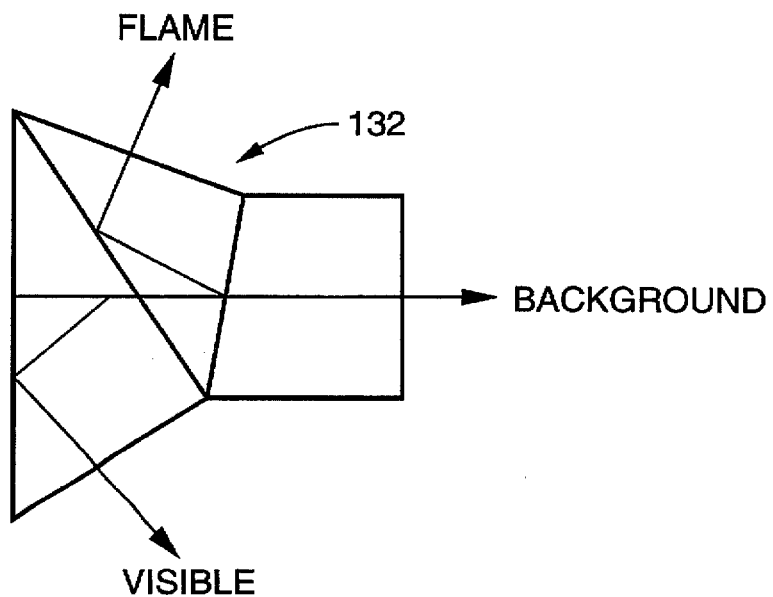
FIG. 7 is a functional schematic diagram showing an alternative embodiment of the beam splitting optics shown in FIG. 6.

Referring now to FIG. 6, there is shown an example of a preferred embodiment of the optics used to separate the incoming light into the three components described above which are used to cream the camera image. A commercial 35-mm single reflex lens 100 or the like is used to acquire the light from the scene to be imaged. A cold mirror at surface 112 separates the visible color spectral image from the IR images. The mirror at this surface transmits light above approximately 650 nm and reflects light from approximately 400 to 650 nm. The light in the 400–650 nm band is reflected to surface 114, which is a highly reflective mirror. This surface produces a second reflection of the visible beam to produce a normal image. The visible light reflected from surface 114 is imaged with a color or monochrome CCD array 116 to create the visible image. In this regard, it is preferable to use first surface mirrors so that this image will be aberration free.

The IR light transmitted through the cold mirror surface 112 enters a prism 118 containing a broadband beam splitter at surface 120. Since the background (background only) wavelength band is a region where the CCD spectral sensitivity is much greater than the flame band and the background band encompasses a wider wavelength region, a 10–90 split provides an adequate background signal and strong flame signal. Roughly 10% of the image in the approximately 900 to 1200 nm range is reflected to surface 122, another high reflectance mirror, resulting in a normal background image. The light reflected from surface 122 is then passed through a trim filter 124. Trim filter 124 is centered at approximately 1050 nm with a half width of approximately 70 nm isolates the wavelengths selected for the background image. The light passing through trim filter 124 is then imaged with a monochrome CCD array 126.

The 90% band transmitted through the broadband beam splitter 120 goes to form the combined flame/background image. A trim filter 128 with a center wavelength of approximately 1130 nm and half width of approximately 60 nm is used to isolate the wave band with the optimal flame signal content. The light passing through trim filter 128 is then imaged with a monochrome CCD array 130.

As discussed previously, the background (background only) and flame (background and flame) signals will be compared in order to detect those pixels where the flame signal intensity is larger than the background, indicating the presence of a flame. However, due to the differences in the amount of light available in the two signals' pass bands and in the CCDs that will measure them, the flame and background signals will likely show a baseline offset when there is no flame present. Therefore, apparatus preferably includes means to adjust the array gains to compensate for this offset before any comparison is made for flame detection. This adjustment and other processing is performed by the camera electronics as described below.

It will be appreciated that the configuration of optics shown in FIG. 6 has several advantages, chief among them being ease of manufacture and adaptability to other spectral ranges. However, a alternative embodiment uses the prism optics shown in FIG. 7. This type of prism 132 is commonly used in broadcast CCD cameras to separate the three color bands, red, green, and blue for imaging on separate arrays. If the prism surfaces are coated with the proper coatings, this configuration can also be used to separate the flame, background, and visible images as described above.

4. Processing Electronics

Figure 8:
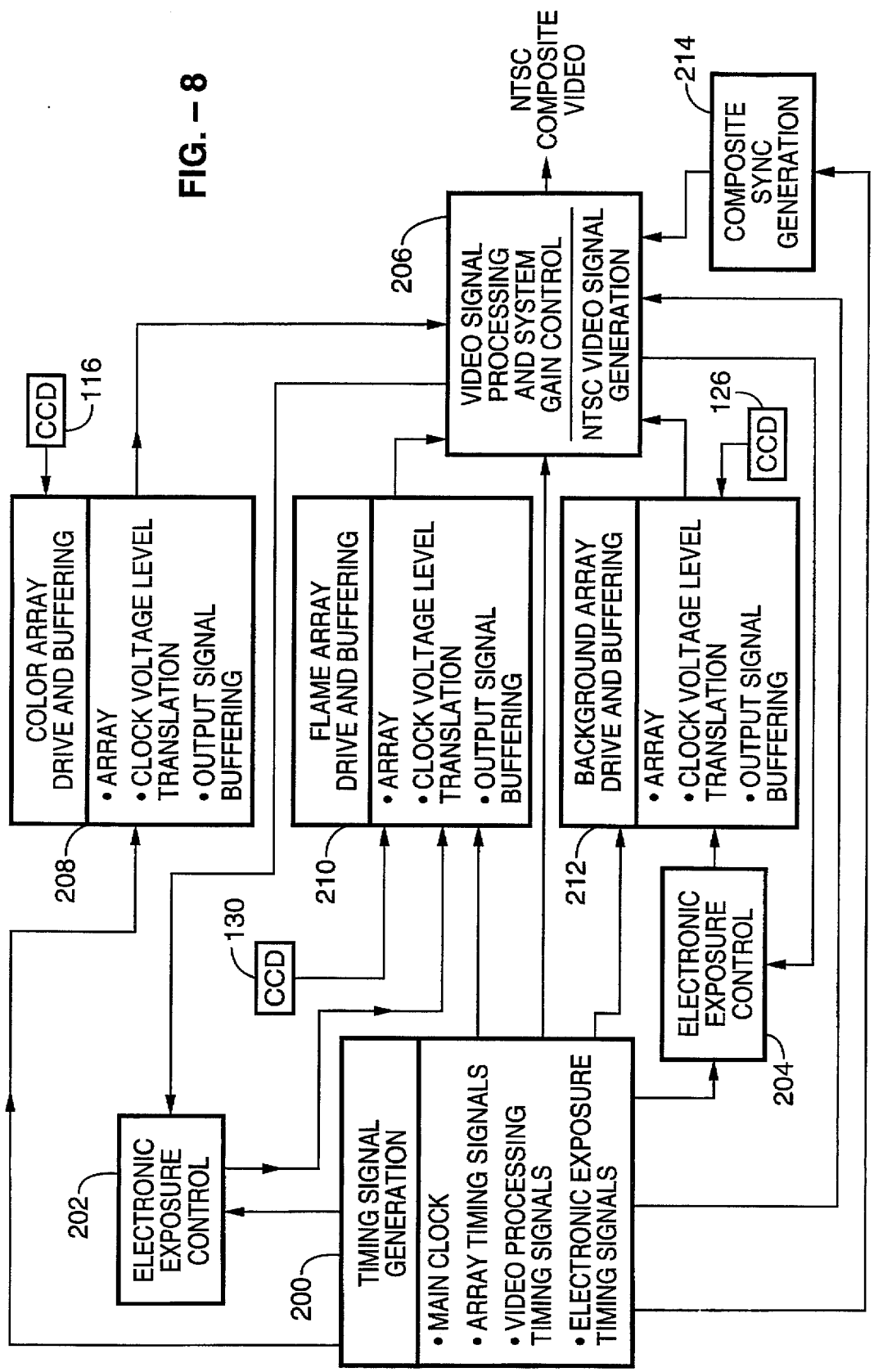
FIG. 8 is a functional block diagram of the image processing circuity in accordance with the present invention.

Referring to FIG. 8, a functional block diagram of the camera electronics of the present invention is shown. In essence, many of the functional elements are similar to those necessary to drive any conventional CCD based camera. However, additional circuits are required to perform the system gain control, image processing, and image overlay for the three separate images acquired.

A master timing circuit 200 generates all clocks and control signals needed to drive the three CCD arrays. The electronic exposure controls 202, 204 generate reset signals that clears the pixel sites in the arrays. By controlling the time at which the reset occurs, the integration period of the array can be varied, effecting the exposure of the resulting image. The system gain control portion of processor 206 compares the relative levels of the flame and background signals and adjusts the inputs to the electronic exposure controls to achieve the best match between the flame and background baseline signals. The array drive and buffering circuits 208, 210, 212 receive the image signals from CCDs 116, 126 and 130, perform level shifting of the timing signals to the match the array requirements, and buffer the array outputs. The video signal processing portion of processor 206 performs the required image processing to extract the flame image and overlay it on the color image. The composite sync generation circuit 214 generates the timing signals that are mixed with the video output to generate NTSC composite video.

It will be appreciated that the exposure of an image generated by a CCD array is determined by the integration time. Integration time is the period during which the array photosites accumulate charge which is proportional to the incident light on the array. Low light level conditions require long integration times, while high light levels require shorter times. Under conditions of maximum integration time, the photosites start accumulating charge at the beginning of each field immediately following the vertical blanking interval. The charge is transferred from the photosites to the storage area during the next vertical blanking interval and the cycle repeats. Integration time is controlled by varying the time interval during which the photosites accumulate charge. This is accomplished by resetting the photosites at a point in time after the start of a field thereby allowing the photosites to accumulate charge for only a portion of the field time. The new integration time is then defined by the interval between the reset pulse and the next vertical blanking interval. Optimization of the integration time is critical for the best use of the available light for flame image extraction.

The use of two arrays presents a unique problem in that a relationship between the array integration times must be established and maintained even though the relationship may not be linear. This implies that one array is the master and the other the slave. In the present invention, it has been found preferable to define the background image array as the master with the flame array being the slave. Note, however, that there is a need to determine when a change to the integration time of an array is required. For purposes of this disclosure, this is referred to as "white level detection".

White level detection determines if a change to the integration time is required, for the background array, by comparing the number of pixels having a whim signal response greater than a predefined level to a predetermined count. When the number of pixels exceeding the comparison level is equal to or greater than the specified count, a signal is generated to cause a decrease in the integration time. In the present invention, the white level detection circuit is preferably implemented with a conventional comparator that compares the background array signal to a reference voltage level which is a specific fraction of the array saturation voltage. When a pixel signal level is greater than the reference voltage, the comparator output clocks a counter. In this manner, the number of pixels that exceed the reference level are counted. If the count is less than the predetermined number, a signal is generated to increase the integration time. If the count is greater than the predetermined number, a signal is generated to cause a decrease in integration time. The pixel counter can be reset at the end of each line or each field. This allows control of the integration time period to be based on the content of a single line or an entire field.

Accordingly, it will be seen that this invention provides for accurate and economical detection of spectral emissions which are not normally visible to the human eye. Although the description above contains many specificities, these should not be construed as limiting the scope of the invention but as merely providing illustrations of some of the presently preferred embodiments of this invention. Notably, the camera design described above can be adapted for other spectral imaging applications. Since the wavelengths measured by the flame and background CCD arrays are determined by trim filters that are easily replaced, the wave bands measured by the camera can be varied. For example, the camera described above can be used to perform imaging used in the early detection of plant stress. Current research indicates that measurements of leaf reflectance at a narrow band centered at 694 nm, divided by a background measurement at 790–800 nm can indicate damage to the chlorophyll in a plant long before any visible evidence is detected. By simply changing the trim filters used in the design above, the camera can be used to make these measurements. It may even be desirable to place a series of filters on a fixture that can be moved through the camera, allowing user selection of the filters used. Additionally, the invention could be used for two-color imaging radiometer temperature measurements by (i) replacing the flame and background trim filters with appropriate bandpass filters and imaging two spectral bands, (ii) taking the ratio of the image signals, (iii) processing the ratioed signals to determine temperature, (iv) overlaying the temperature measurement onto a color image, and (v) using the overlay colors to designate temperature ranges. Alternatively, the invention could be used as a single-color imaging ratiometer with background compensation by (i) imaging two spectral bands, (ii) subtracting the shorter wavelength image from the longer wavelength image to remove non-thermal components, (iii) digitizing and measuring the intensity of the thermal image regions, and (iv) overlaying the temperature data on the color image. Thus the scope of this invention should be determined by the appended claims and their legal equivalents.

What is claimed is:

1. A flame detection method, comprising the steps of:
   (a) acquiring light emissions from an area to be viewed;
   (b) separating said acquired light emissions into first, second and third beams of light, said first beam comprising light having a wavelength corresponding to combined flame and background emissions, said second beam comprising light have a wavelength corresponding to background emissions, said third beam comprising visible light emissions;
   (c) imaging said first, second and third beams of light to produce flame plus background, background, and visible images;
   (d) subtracting said background image from said background flame image to produce a flame image; and
   (e) superimposing said flame image onto said visible image.

2. A method for detecting flames which are not visible to the human eye, comprising the steps of:
   (a) acquiring light emissions from an area to be viewed;
   (b) separating said acquired light emissions into first, second and third beams of light, said first beam comprising light having a wavelength corresponding to combined flame and background emissions, said second beam comprising light having a wavelength corresponding to background emissions, said third beam comprising visible light emissions;
   (c) imaging said first, second and third beams of light to produce flame plus background, background, and visible images;
   (d) extracting a flame image from said background plus flame image; and
   (e) superimposing said flame image onto said visible image.

3. A method as recited in claim 2, wherein said step of extracting a flame image from said background plus flame image comprises the steps of:
   (f) comparing pixels in said background plus flame image with corresponding pixels in said background image;
   (g) designating a pixel in said background plus flame image as a flame image pixel if said pixel has a greater amplitude than said corresponding pixel in said background image.

4. A method as recited in claim 3, further comprising the step of producing a flame image video output signal dependent upon the number of consecutive flame image pixels.

5. A flame detection method, comprising the steps of:
   (a) acquiring light emissions from an area to be viewed;
   (b) separating said acquired light emissions into first, second and third beams of light, said first beam comprising light having a wavelength corresponding to combined flame and background emissions, said second beam comprising light have a wavelength corresponding to background emissions, said third beam comprising visible light emissions;
   (c) imaging said first, second and third beams of light to produce flame plus background, background, and visible images;
   (d) comparing pixels in said background plus flame image with corresponding pixels in said background image;
   (e) designating a pixel in said background plus flame image as a flame image pixel if said pixel has a greater amplitude than said corresponding pixel in said background image; and
   (f) superimposing said flame image pixels onto said visible image.

6. A method as recited in claim 5, further comprising the step of producing a flame image video signal dependent upon the number of consecutive flame image pixels.

7. A flame detection apparatus, comprising:
   (a) means for acquiring light emissions from an area to be viewed;
   (b) means for separating said acquired light emissions into first, second and third beams of light, said first beam comprising light having a wavelength corresponding to combined flame and background emissions, said second beam comprising light have a wavelength corresponding to background emissions, said third beam comprising visible light emissions;
   (c) means for imaging said first, second and third beams of light to produce flame plus background, background, and visible images;
   (d) means for subtracting said background image from said background flame image to produce a flame image; and
   (e) means for superimposing said flame image onto said visible image.

8. An apparatus for detecting flames which are not visible to the human eye, comprising:
   (a) means for acquiring light emissions from an area to be viewed;
   (b) means for separating said acquired light emissions into first, second and third beams of light, said first beam comprising light having a wavelength corresponding to combined flame and background emissions, said second beam comprising light have a wavelength corresponding to background emissions, said third beam comprising visible light emissions;
   (c) means for imaging said first, second and third beams of light to produce flame plus background, background, and visible images;
   (d) means for extracting a flame image from said background plus flame image; and
   (e) means for superimposing said flame image onto said visible image.

9. An apparatus as recited in claim 8, wherein said means for extracting a flame image from said background plus flame image comprises:
   (a) means for comparing pixels in said background plus flame image with corresponding pixels in said background image;
   (b) means for designating a pixel in said background plus flame image as a flame image pixel if said pixel has a greater amplitude than said corresponding pixel in said background image.

10. An apparatus as recited in claim 9, further comprising means for producing a flame image video output signal dependent upon the number of consecutive flame image pixels.

11. A flame detection apparatus, comprising:
   (a) means for acquiring light emissions from an area to be viewed;
   (b) means for separating said acquired light emissions into first, second and third beams of light, said first beam comprising light having a wavelength corresponding to combined flame and background emissions, said second beam comprising light have a wavelength corresponding to background emissions, said third beam comprising visible light emissions;

(c) means for imaging said first, second and third beams of light to produce flame plus background, background, and visible images;

(d) means for comparing pixels in said background plus flame image with corresponding pixels in said background image;

(e) means for designating a pixel in said background plus flame image as a flame image pixel if said pixel has a greater amplitude than said corresponding pixel in said background image; and (f) means for superimposing said flame image pixels onto said visible image.

12. A method as recited in claim 11, further comprising means for producing a flame image video signal dependent upon the number of consecutive flame image pixels.

* * * * *